US007998461B2

(12) United States Patent
Forbes et al.

(10) Patent No.: US 7,998,461 B2
(45) Date of Patent: Aug. 16, 2011

(54) *SALMONELLA* CANCER THERAPEUTICS AND RELATED THERAPEUTIC METHODS (75) Inventors: Neil S. Forbes, Belchertown, MA (US); Rachel W. Kasinskas, East Kingston, NH (US)

(73) Assignee: University of Massachusetts, Boston, MA (US)

( * ) Notice: Subject to any disclaimer, the term of this patent is extended or adjusted under 35 U.S.C. 154(b) by 170 days.

(21) Appl. No.: 12/313,052

(22) Filed: Nov. 17, 2008

(65) Prior Publication Data

US 2009/0175829 A1 Jul. 9, 2009

Related U.S. Application Data

(60) Provisional application No. 61/003,199, filed on Nov. 15, 2007.

(51) Int. Cl.
*A61K 49/00* (2006.01)
*A61K 39/112* (2006.01)
*C07H 21/04* (2006.01)

(52) U.S. Cl. ........ 424/9.2; 424/9.1; 424/93.1; 424/93.2; 424/234.1; 424/258.1; 435/41; 435/69.1; 435/440; 536/23.1; 536/23.7

(58) Field of Classification Search .................... 424/9.1, 424/9.2, 93.1, 93.2, 234.1, 258.1; 435/41, 435/69.1, 440; 536/23.1, 23.7
See application file for complete search history.

(56) References Cited

U.S. PATENT DOCUMENTS

| 6,080,849 | A | 6/2000 | Bermudes et al. |
|---|---|---|---|
| 6,447,784 | B1 | 9/2002 | Bermudes et al. |
| 6,475,482 | B1 | 11/2002 | Bermudes et al. |
| 6,863,894 | B2 | 3/2005 | Bermudes et al. |
| 6,923,972 | B2 | 8/2005 | Bermudes et al. |
| 6,962,696 | B1 | 11/2005 | Bermudes et al. |
| 7,015,027 | B1 | 3/2006 | Redshaw |
| 7,247,296 | B2 | 7/2007 | Redshaw |
| 7,354,592 | B2 | 4/2008 | Bermudes et al. |
| 7,514,089 | B2 | 4/2009 | Bermudes et al. |
| 2006/0104955 | A1 | 5/2006 | Redshaw |

OTHER PUBLICATIONS

Pawelek, J.M. et al. Bacteria as tumour-targeting vectors. The Lancet Oncology. vol. 4, pp. 548-556, Sep. 2003.*
Kasinskas, R.W. et al. *Samonella typhimurium* specifically chemotax and proliferate in heterogenous tumor tissue in vitro. Biotechnology and Bioengineering, vol. 94, No. 4, Jul. 2006.*
Kasinskas, RW; Forbes, NS. *Salmonella typhimurium* Lacking Ribose Chemoreceptors Localize in Tumor Quiescence and Induce Apoptosis. Cancer Res. 2007; 67: (7), Apr. 1, 2007, pp. 3201-3209.
Clairmont, C., et al., "Biodistribution and Genetic Stability of the Novel Antitumor Agent VNP20009, a Genetically Modified Strain of *Salmonella typhimurium*," *The Journal of Infectious Diseases* 181:1996-2002 (2000).
Cunningham, C. and Nemunaitis, J., "A Phase I Trial of Genetically Modified *Salmonella typhimurium* Expressing Cytosine Deaminase (TAPET-CD), VNP20029) Administered by Intratumoral Injection in Combination With 5-fluorocytosine for Patients With Advanced or Metastatic Cancer," Protocol No. CL-017, Version: Apr. 9, 2001. 12:1594-1596 (2001).
Forbes, N.S., et al., "Sparse Initial Entrapment of Systemically Injected *Salmonella typhimurium* Leads to Heterogeneous Accumulation Within Tumors," Cancer Research 63:5188-5193 (2003).
King, I, et al., "Tumor-Targeted *Salmonella* Expressing Cytosine Deaminase as an Anticancer Agent," *Human Gene Therapy* 13:1225-1233 (2002).
Lee, K.C., et al., "Evaluation of the Acute and Subchronic Toxic Effects in Mice, Rats, and Monkeys of the Genetically Engineered and *Escherichia coli* Cytosine Deaminase Gene-Incorporated *Salmonella* Strain, TAPET-CD, Being Developed as an Antitumor Agent," *International Journal of Toxicology* 20:207-217 (2001).
Low, K.B., et al., Construction of VNP20009, "A Novel, Genetically Stable Antibiotic-Sensitive Strain of Tumor-Targeting *Salmonella* for Parenteral Administration in Humans," *Methods in Molecular Medicine 90, 47-59 Suicide Gene Therapy: Methods and Reviews,* Ed. C.J. Springer, Humana Press.
Low, K.B., et al., "Lipid a Mutant *Salmonella* With Supressed Virulence and TNFα Induction Retain Tumor-Targeting in Vivo," *Nature Biotechnology* 17:37-41 (1999).
Luo, X., et al., "Genetically Armed *Salmonella typhimurium* Delivered Therpauetic Gene and Inhibited Tumor Growth in Preclinical Models," *Proc Annu Meet Am Assoc Cancer Res* 42: Abs 3693 (2001).
Luo, X., et al., "Antitumor Effect of VNP20009, an Attenuated *Salmonella*, in Murine Tumor Models," *Onoclogy Research* 12:501-508 (2002).
Mei, S., et al., "Optimization of Tumor-Targeted Gene Delivery by Engineered Attenuated *Salmonella typhimurium*," *Anticancer Research* 22:3261-3266 (2002).
Michl, P. and Gress, T.M., "Bacteria and Bacterial Toxins as Therapeutic Agents for Solid Tumors," *Current Cancer Drug Targets* 4:689-702 (2004).
Nemunaitis, J., et al., "Pilot Trial of Genetically Modified, Attenuated *Salmonella* Expressing the *E. coli* Cytosine Deaminase Gene in Refractory Cancer Patients," *Cancer Gene Therapy* 10:737-744 (2003).
Pawelek, J.M., et al., "Tumor Targeted *Salmonella* as a Novel Anticancer Vector," *Cancer Research* 57:4537-4544 (1997).
Toso, J.F., et al., "Phase I Study of the Intravenous Administration of Attenuated *Salmonella typhimurium* to Patients With Metastatic Melanoma," *J. Clin. Oncol.* 20(1):142-152 (2001).
Yu, Y.A., et al., "Visualization of Tumors and Metastases in Live Animals With Bacteria and Vaccinia Virus Encoding Light-Emitting Proteins," *Nature Biotechnology* 22(3):313-320 (2004).
Zhao, M., et al., "Targeted Therapy with a *Salmonella Typhimurium* Leucine-Arginine Auxotroph Cures Orthotopic Human Breast Tumors in Nude Mice," *Cancer Res.* 66(15):7647-7652 (2006).
Zhao, M., et al., "Tumor-Targeting Bacterial Therapy With Amino Acid Auxotrophs of GFP-Expressing *Salmonella typhimurium*," *PNAS* 102(3):755-760 (2005).
Zheng, L., et al., "Tumor Amplified Protein Expression Therapy: *Salmonella* as a Tumor-Selective Protein Delivery Vector," *Oncology Research* 12:127-135 (2000).

* cited by examiner

*Primary Examiner* — Rodney P. Swartz

(74) *Attorney, Agent, or Firm* — Hamilton, Brook, Smith & Reynolds, P.C.

(57) ABSTRACT

Therapeutic methods for treatment of solid tumor cancer cell masses, as can be effected using therapeutic compositions comprising *Salmonella* species/strains and related compositions.

20 Claims, 6 Drawing Sheets

SALMONELLA CANCER THERAPEUTICS AND RELATED THERAPEUTIC METHODS

This application claims priority benefit from application Ser. No. 61/003,199 filed Nov. 15, 2007, the entirety of which is incorporated herein by reference.

BACKGROUND OF THE INVENTION

The use of bacteria to treat cancer has been investigated for well over 150 years, and many genera of bacteria, including *Clostridium, Bifidus*, and *Salmonella*, have been shown to preferentially accumulate in tumor tissue and cause regression. The efficacy of such standard therapeutic strategies is limited because quiescent cancer cells can begin to proliferate and repopulate the tumor between courses of chemotherapy. The inability to completely kill all cancer cells following a single course of chemotherapy allows more time for individual cells to intravasate into blood vessels, increasing the chance of metastasis. Multi-drug resistance was observed over time, and bacterial therapies were reconsidered. Motile, nonpathogenic bacteria were believed to have the potential to overcome multi-drug resistance, with tumor penetration into quiescent cellular regions more effectively than otherwise possible using passively diffusing drug molecules.

Bacterial treatments expanded with the discovery of strains that specifically target tumor tissue. For instance, nonpathogenic *Clostridium butyricum* was used for the treatment of malignant brain tumors in mice. Intravenous injections caused noticeable regression due to accumulation in necrotic tumor regions. However, while complete regression of large tumors was observed, small tumors were unaffected. Moreover, the rate of recurrence was also unchanged, and animal death was imminent in all cases studied. The inability of *Clostridia* to alter rate of tumor recurrence is believed to directly relate to the fact that colonization of the tumor necrosis leaves a rim of viable cells at the tumor periphery. Even if lysis occurs, permanent eradication is not always guaranteed, as viable cells can continue to grow and ultimately repopulate the tumor.

An alternate approach became available through recombinant technologies. *Clostridia* were engineered into tumor-targeting vectors capable of delivering cytokines or prodrug-converting enzymes to poorly-perfused tumor regions. Anti-cancer therapeutics could then be produced locally within specific tumor regions, overcoming many of the diffusion limitation of systemically-administered chemotherapeutics. As an example, the cytosine diaminase gene of *E. coli* was cloned into a clostridial expression vector and transfected into *C. biejerincki*. In vitro assays showed that the bacteria were capable of producing high levels of the active *E. coli* derived enzyme. Used in combination, cytosine deaminase-expressing bacteria could be used to incite conversion of the non-toxic prodrug 5-fluorocytosine (5-FC) into the active chemotherapeutic agent 5-fluorouracil (5-FU) within specific tumor regions.

The use of *Salmonella typhimurium* to treat solid tumors began with the development of a nonpathogenic strain, VNP20009. Well-tolerated in mice and humans, this strain has been shown to preferentially accumulate (>2000-fold) in tumors over the liver, spleen, lung, heart and skin, retarding tumor growth between 38-79%, and prolonging survival of tumor-bearing mice. In initial clinical trials, *S. typhimurium* was found to be tolerated at high dose and able to effectively colonize human tumors.

Several strains of *Salmonella* have also been genetically modified to express the *E. coli* cytosine deaminase enzyme (TAPET-CD). When tumor-bearing mice were administered 5-FC in conjunction with VNP20009, accumulation of bacteria was 1000-fold higher than in normal tissue and tumor, and growth inhibitions of 88-96% were achieved. A pilot study on three refractory cancer patients was performed to test the accumulation and therapeutic affect of TAPET-CD in human patients. Proof of concept was demonstrated by the intratumoral conversion of 5-FC to 5-FU, demonstrating that *Salmonella* has inherent anti-tumor activity and the ability to deliver therapeutic enzymes and proteins to solid tumors in vivo. However, control over localization was not achieved and most *Salmonella* strains tend to colonize necrotic, rather than quiescent, regions.

SUMMARY OF THE INVENTION

In light of the foregoing, it is an object of the present invention to provide various therapeutic methods and/or compositions directed to the use of bacteria to treat cancer disease states, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to provide a method of using chemotaxis to direct bacterial tumor accumulation.

It can be another object of the present invention to selectively eliminate one or more chemoreceptor genes from therapeutic strains of one or more *Salmonella* species.

It can also be an object of the present invention to provide a method to control bacterial accumulation of such a strain in a quiescent region of a tumor or cell mass.

It can also be an object of the present invention, alone or in conjunction with one or more of the preceding objectives, to provide one or more methods and/or compositions for the treatment of solid tumor cancers.

Other objects, features, benefits and advantages of the present invention will be apparent from the summary and the following descriptions of certain embodiments, and will be readily apparent to those skilled in the art having knowledge of various bacterial therapeutic techniques and/or treatments. Such objects, features, benefits and advantages will be apparent from the above as taken into conjunction with the accompanying examples, data, figures and all reasonable inferences to be drawn therefrom, alone or with consideration of the reference incorporated herein.

In part, the present invention can be directed to a method of treating, inhibiting growth and/or reducing mass or volume of a solid tumor cancer. Such a method can comprise contacting a mass of cancer cells with an effective amount of a non-pathogenic mutant *Salmonella* species, such as a mutant *Salmonella* species absent a gene (e.g., trg) for tumor necrosis chemoreception and/or, for example, comprising a genetically-modified ribose/galactose receptor (e.g., a Trg chemoreceptor), wherein said knock-out strain is capable of chemotaxis to and/or accumulation in a quiescent region of such a cell mass or a particular region thereof. As used herein and as would be understood by those skilled in the art, the term "treatment" can refer to any affect on a cancer cell, cellular mass and/or tumor in conjunction with use of the present invention, such affect as can result in adverse cell impact including but not limited to inhibited cell growth or cell death. "Contacting" means that the subject cellular mass and the *Salmonella* species are brought together, regardless of mode of administration, such that the *Salmonella* species can chemotax to the cellular mass or a particular region thereof. In light of the present specification, such contacting would be understood by those skilled in the art made aware of this invention. In certain embodiments, in conjunction with such a method, such treatment, inhibition and/or volume reduction can be evidenced by induction of and/or increased apoptosis, as compared to that resulting from a strain without the trg knockout, and as can be measured by an increase in caspase-3 activity. Regardless, in certain embodiments, such a mutant *Salmonella* species can be derived from nonpathogenic strains of *S. typhimurium*. A non-pathogenic strain can be as would be understood by those skilled in the art. For instance, without limitation, non-pathogenic strains are as described in U.S. Pat. No. 6,962,696 (e.g., single gene knockout), U.S. Pat. No. 6,863,894 (e.g.,double gene knockout), U.S. Pat. Nos. 7,247,296 and 7,015,027, each of which is incorporated herein by reference in its entirety, and any such strain as can be genetically-modified as described herein, for chemotaxis to and/or accumulation in a quiescent region of such a cell/tumor mass. As described more fully below, such a strain can be absent an active trg gene and characterized by the absence of an active Trg chemoreceptor.

As would be understood by those skilled in the art, a method of this invention can be used in vivo. In certain such embodiments, the contacted cell mass can be a human solid tumor cancer characterized, as would be understood in the art, by various ribose and galactose necrotic cell degradation products, such cancers selected from but not limited to lung, colon, liver, kidney, prostate, breast, pancreatic, ovarian, bladder, kidney, thyroid and skin cancers. Accordingly, in such embodiments, a corresponding tumor can be inoculated with a mutant *Salmonella* species, using techniques and protocols as would be understood by those skilled in the art entrusted with the care and treatment of such an individual.

Accordingly, the present invention can also be directed to a pharmaceutical composition, as can be used in conjunction with the method(s) of this invention. As described above, such a composition can comprise a non-pathogenic mutant *Salmonella* species comprising a genetically-modified chemoreceptor knock-out strain (e.g., without limitation, absent an active Trg chemoreceptor) capable of chemotaxis to and/or accumulation in the quiescent region of a tumor or cell mass, and a pharmaceutically-acceptable carrier component. Such a composition can be administered alone or as an adjunct to another therapy selected from chemotherapy, radiation, immunotherapy, gene therapy and/or other cancer therapeutics or vaccines.

Such compositions can comprise admixture with a pharmaceutical diluent or a carrier component of the sort conventionally used in conjunction with such compositions. Without limitation, such pharmaceutical compositions can comprise a diluent or carrier component suitable for use in conjunction with such a therapeutic bacterial species or strain, such a diluent/carrier including but not limited to water, an aqueous medium or a physiological saline solution compatible with one or more modes of administration. Such compositions can be employed at effective daily or periodic dosage levels, such levels, compositions and/or formulations thereof as would be understood by those skilled in the art made aware of this invention.

In part, the present invention can also be directed to a method of controlling location of bacterial accumulation in a solid tumor cancer. Such a method can comprise providing a solid tumor cancer cellular mass comprising proliferating quiescent and necrotic regions; providing a mutant *Salmonella* species, such a species non-pathogenic and absent an active chemoreceptor gene for chemotaxis to a specific tumor region; and contacting the cellular mass with the *Salmonella* species for a time at least partially sufficient for chemotaxis to and/or accumulation of said species in a tumor mass region, such accumulation controlled by the absence of such an active chemoreceptor gene. In certain embodiments (e.g., in vitro), in conjunction with such a methodology, accumulation in and/or apoptosis of the tumor mass can be greater than that evidenced by a wild-type *Salmonella* species lacking the chemoreceptor gene knockout, using techniques of the sort described herein.

In certain embodiments, as discussed above, such a mutant *Salmonella* species can be derived from nonpathogenic strains of *S. typhimurium*. In certain embodiments, such a strain can be absent an active trg gene, and such a mutant *Salmonella* species can accumulate in a quiescent region of the cellular mass. Such a methodology can comprise continued chemotaxis to such a quiescent region, and ongoing in vivo contact and/or bacterial accumulation can be part of or adjunct to an associated treatment of a human solid tumor cancer.

BRIEF DESCRIPTION OF THE DRAWINGS

FIGS. 1A-D. A, schematic representation of the chemotaxis machinery of *S. typhimurium*, including four chemoreceptors (Tar, Tsr, Trg, and Tcp), signal transduction proteins (CheW, CheA, and CheY), flagellar motor (Mot), and flagellar assembly (Fla). The enzymes CheA, a histidine kinase, and CheY, a response regulator, control bacterial chemotaxis by directing flagellar rotation in response to chemoattractant binding. When an attractant molecule binds one of the chemoreceptors, the cytoplasmic region of the receptor inhibits autophosphorylation of CheA, which reduces the phosphorylation of CheY. Phosphorylated CheY induces clockwise flagellar rotation and bacterial "tumbling." In an increasing chemoattractant gradient, the concentration of phosphorylated CheY decreases, the frequency of flagella switching decreases, and the bacterium "runs" up the gradient. B, chemotactic ability ($N/N_{Null}$) of the *S. typhimurium* mutants toward serine (Ser), aspartate (Asp), ribose (Rib), and galactose (Gal) for the wild-type (WT) and the chemotaxis surface receptor knockouts tsr, tar, and trg; the nonmotile and flagellated mot and the nonflagellated fla mutants; and the signal transduction protein knockouts cheY and cheA. Nine replicate capillary assays were done for each mutant-chemoattractant pair. C, accumulation pattern of WT, GFP-expressing *S. typhimurium* in a 930-Am-diameter tumor cylindroid at 13 and 24 h after inoculation. At 13 h, a ring had accumulated at the cylindroid periphery, and at 24 h, bacteria had accumulated in the central necrotic region. D, fluorescent microscopy images showing that the following mutants did not accumulate in tumor cylindroids at 24 h after inoculation: a nonflagellated mutant (fla; n=10), a nonmotile and flagellated mutant (mot; n=6), a cheY mutant (n=9), and a cheA mutant (n=7). No bacteria were observed chemotaxing toward or accumulating in the cylindroids (n=32).

FIGS. 2A-D. A, representative time-lapse fluorescent microscopy images of the accumulation pattern of a tar mutant of *S. typhimurium* in a 1,000-μm-diameter tumor cylindroid at 16 and 34 h after inoculation. The bacteria did not form a ring at 16 h and did not accumulate inside the cylindroids at 34 h. B, a temporal intensity profile within two regions outside of the cylindroids: a 400 μm$^2$ area in the bulk>200 μm from the cylindroid edge and an annulus 200

µm thick around the cylindroid edge. Intensities were averaged across multiple cylindroids (n=4). C, accumulation pattern of WT *S. typhimurium* in tumor cylindroids with a bulk concentration of 5, 1, and 0 mmol/L of added aspartate at 17 h, 10 min, and 29 h after inoculation. D, bulk concentration of aspartate released from colon carcinoma cells in tumor spheroid culture at 0, 24, and 42 h (n=3).

DETAILED DESCRIPTION OF CERTAIN EMBODIMENTS

As can relate to certain embodiments of this invention, it was reasoned that individual chemoreceptors target *S. typhimurium* to specific regions of tumors by controlling their chemotaxis toward specific tumor microenvironments and, more specifically, that *S. typhimurium* targeted to quiescence could induce apoptosis. To demonstrate such aspects of this invention, timelapse fluorescent microscopy was used to quantify the accumulation pattern of a series of chemotaxis machinery knockouts in tumor cylindroids. Cylindroids are an in vitro tumor model, understood and acknowledged by those skilled in the art, to mimic the microenvironments and metabolite gradients in human tumors. The extent of apoptosis was measured using a stain that binds to activated caspase-3. From the accumulation pattern of knockouts in cylindroids, the role of each chemotaxis component on the chemotaxis of *S. typhimurium* toward different tumor regions was determined. The tested strains included three cell surface chemoreceptor knockouts (tsr, tar, and trg), a flagella knockout (fla), a motor assembly knockout (mot), and two signal transduction knockouts (cheA and cheY). The chemoreceptor knockouts are not attracted to serine (tsr), aspartate (tar), and ribose/galactose (trg). The knockouts lacking the flagella (fla) and motor assemblies (mot) are nonmotile, and knockouts lacking the signal transduction proteins (cheA and cheY) are motile but do not respond to chemoattractant gradients.

The results obtained confirm that chemotaxis is related to bacterial accumulation in tumors and that the individual chemoreceptors can play independent roles in directing *S. typhimurium* to different microenvironment regions of tumors. Determining the roles of each chemoreceptor and the chemotaxis machinery is an important step in the development of bacterial therapies that are able to target the therapeutically inaccessible regions of tumors.

Chemotaxis deficiency in mutant *S. typhimurium*. More specifically, with reference to Example 1, the needle-syringe assay was done with the chemotaxis machinery mutants to determine their relative attraction to the known *S. typhimurium* attractants (FIG. 1B). Chemotactic ability is reported as the average number of bacteria in the chemoattractant containing capillaries compared with the average number of bacteria in the control capillaries (N/NNull). A N/NNull ratio of ≦1.0 indicates that bacterial movement is driven by random motility and not by specific chemotaxis. As expected, the WT was attracted to aspartate, serine, ribose, and galactose, and the chemoreceptor knockouts (tsr, tar, and trg) were not attracted to their corresponding chemoattractants (serine, aspartate, and ribose/galactose; P<0.05; FIG. 1B). The strains with mutations in the flagellar machinery (mot and fla) and the chemotaxis signal transduction pathway (cheA and cheY) had decreased chemotactic ability toward all of chemoattractant molecules compared with the WT (FIG. 1B), confirming the reported necessity of these proteins for chemotaxis.

WT accumulation in cylindroids. The accumulation of each mutant strain in cylindroids was compared with the accumulation of WT *S. typhimurium* as a control. As previously observed, the WT penetrated into the periphery of cylindroids at early times (13 h) and formed a ring of bacteria (FIG. 1C). At later times (24 h), bacteria accumulated in the necrotic center of the cylindroids (FIG. 1C). During this time, individual *S. typhimurium* were observed through the eyepiece actively swimming toward the central region of the cylindroids (data not shown).

Nonmotile and signal transduction pathway mutants do not chemotax toward cylindroids. The nonmotile (fla, n=10 and mot, n=6) and the signal transduction (cheY, n=9 and cheA, n=7) mutants did not form a discernible ring at the cylindroid periphery throughout the course of growth in cylindroid cultures (FIG. 1D), indicating that these mutants are not attracted to cylindroids. Each strain was visibly fluorescent and was observed replicating in cylindroid bulk at rates similar to the WT (data not shown). By visual observation under the microscope, it was confirmed that the cheA and cheY mutants were motile and the fla and mot mutants were not motile in cylindroid cultures (data not shown).

The aspartate receptor is necessary for *S. typhimurium* chemotaxis toward cylindroids. Presence of the Tar receptor is essential for *S. typhimurium* chemotaxis toward tumor cylindroids (FIG. 2A). When inoculated into multiple cylindroids, tar did not form a ring at the peripheral edge of cylindroids at any time points (n=21; FIG. 2A). At early times (16 h), no accumulation was observed at the cylindroid edge (FIG. 2A). At later times (34 h), the concentration of bacteria increased in both the bulk and the peripheral region surrounding the outside of the cylindroids (FIG. 2A). The average fluorescence intensity increased as a function of time within these two regions, indicating that bacteria are actively growing in both the local exterior region (P<0.01; n=4) and the bulk (P<0.01; n=4; FIG. 2B). The lack of an accumulation ring, which was present following inoculation with the WT (FIG. 1C), indicates that tar does not chemotax toward cylindroids. Once flooding of the bulk began to occur, individual bacteria were able to chemotax into large tumor cylindroids and accumulate within the centers (data not shown). This suggests that functionalities of the remaining receptors were preserved in this environment.

The addition of aspartate to the bulk medium confirms that the Tar receptor is the dominant receptor governing external chemotaxis of *S. typhimurium* toward tumor cylindroids (FIG. 2C). Aspartate was added to the bulk medium to eliminate the gradient at the cylindroid outer edge. The presence of a gradient was confirmed by measuring the concentration of aspartate in the bulk medium of spheroid cultures as a function of time (FIG. 2D). Spheroids composed of colon carcinoma cells excrete aspartate at an average rate of $1.0 \times 10^{-13}$ mmol/cell/h. The inhibition of ring formation by WT *S. typhimurium*, which have functional aspartate receptors, shows that chemotaxis is driven by this aspartate gradient (FIG. 2C). When the bulk concentration of aspartate was increased to 5 mmol/L, WT *S. typhimurium* did not form of a ring and did not chemotax toward tumor cylindroids at any time (n=10; FIG. 2C). In comparison, the controls (0 mmol/L added aspartate) formed bacterial rings at the edge of the cylindroids within 17 h (n=9; FIG. 2C). In the 0 mmol/L controls, individual WT bacteria were observed through the eyepiece actively swimming toward the center of the cylindroids at 17 h (data not shown).

The timing of WT *S. typhimurium* chemotaxis toward cylindroids was dependent on the bulk aspartate concentration. At intermediate aspartate concentrations (1 mmol/L), a chemotactic ring formed after a longer period (29 h; n=4; FIG. 2C). This delay suggests that the cancer cells in the cylindroids produced enough aspartate during this time to reestablish a recognizable gradient (FIG. 2C) and that the concentration of aspartate at the cylindroid edge was between 1 and 5 mmol/L.

Figure 3A:
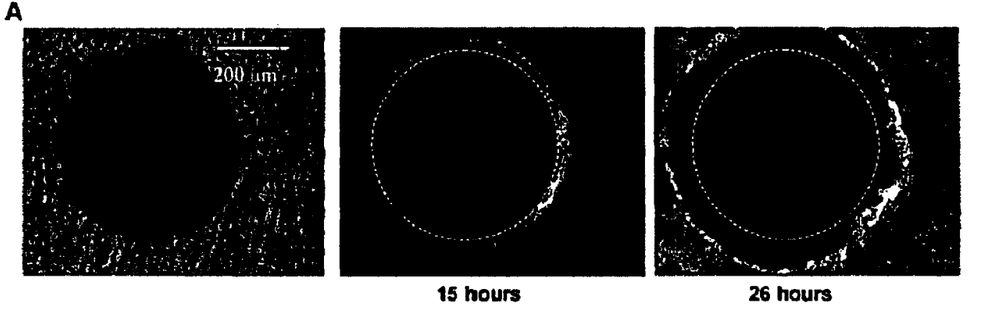
FIGS. 3A-D. A, time-lapse fluorescent microscopy images showing that the tsr mutant did not accumulate at the center of tumor cylindroids at 15 and 26 h after inoculation. The ring of bacteria that formed at the edge moved away from the cylindroid with time. Dashed line, edge of the cylindroid. B, average normalized intensity of bacteria located at the center of the cylindroid (20% of the radius) and within an annulus, 20% thick, inward from the leading edge of the bacterial ring at 15 and 26 h after inoculation. More bacteria were present at the periphery than at the center (P<0.01). C, normalized radial intensity profiles corresponding to the images in (A). Arrows, location of the bacterial ring at 15 and 26 h. D, average increase in the radius of the bacterial ring from 16 to 22 h after inoculation (n=5). The rate was statistically non-zero. *, P<0.01.
Figure 3B:
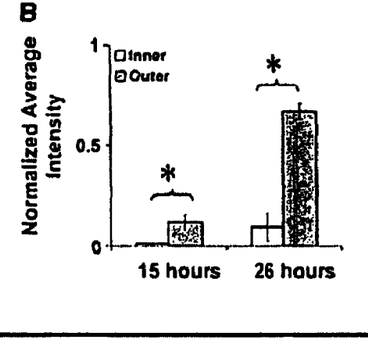

Initiation of *S. typhimurium* penetration into cylindroids is controlled by the Tsr chemoreceptor. The serine receptor mutant tsr chemotaxed toward but did not accumulate in the center of tumor cylindroids (FIG. 3) as shown by the formation of a ring of bacteria at the cylindroid edge (FIG. 3A). The tsr mutant was not observed accumulating in the center of cylindroids up to 30 h after inoculation (n=5; FIG. 3A). At early and late time points (15 and 26 h), the average pixel intensity at the center (the internal 20%) of the observed cylindroids was significantly less than the average intensity at the leading edge of the bacterial ring (P<0.01; n=5; FIG. 3B).

Figure 3C:
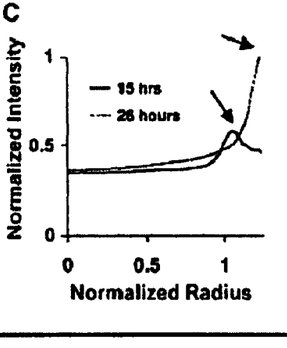

Once the ring of bacteria was established, the bacteria did not move into the cylindroid (FIG. 3C). This behavior was different from the WT strain, which possesses functional Tsr receptors, and accumulated in the center of cylindroids (FIG. 1C).

Figure 3D:
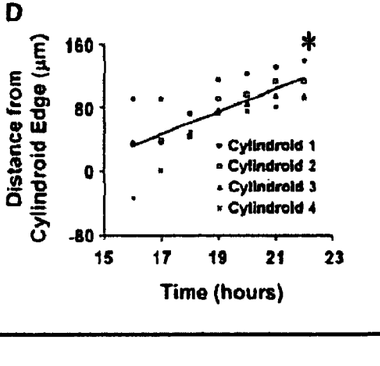

At early time points, the tsr mutant accumulated at the periphery of cylindroids, creating a ring that moved outward from the cylindroids with time (FIG. 3A). Based on the transmitted light images, the radius of the cylindroids did not change throughout the experiments. The cylindroid boundary is indicated by the dashed line in the fluorescence images in FIG. 3A. The outward movement of the bacterial ring is reflected in the radial intensity profiles, where the maximum concentration of bacteria at 15 and 26 h was found at r/R=1.06 and r/R=1.23, respectively (FIG. 3C), where r/R is the radial position normalized by the radius of the cylindroid. The ring of bacteria moved away from all observed cylindroids at 14.4±2.6 μm/h (n=4; FIG. 3D).

Over time, the tsr mutant formed a distinct honeycomb pattern in the bulk (FIG. 3A), which is caused by self-produced aspartate gradients. The outward movement of the bacterial ring and the growth of individual void spaces in tsr cultures may have been caused by similar aggregation mechanisms. The local aspartate gradients around tsr mutants in the bulk may have been greater than the aspartate gradient produced by tumor cells and appear to have pulled the bacteria from the cylindroids into the bulk (FIG. 3A).

Deletion of the Trg receptor induces accumulation in tumor quiescence. Absence of the Trg receptor caused *S. typhimurium* to accumulate in the quiescent region of tumor cylindroids. The trg mutant accumulated in distinct colonies within a broad ring between the outer, proliferating edge (FIG. 4A) and the central apoptotic region of cylindroids (FIG. 5A). Twenty-four hours after inoculation, the average center of mass of each colony was located at r/R=0.74±0.15 (FIG. 4B), which coincides with the location of quiescent cells in tumor cylindroids. (Kasinskas RW, Forbes NS. *Salmonella typhimurium* specifically chemotax and proliferate in heterogeneous tumor tissue in vitro. Biotechnol Bioeng 2006; 94:710-21.) Colonies of the trg mutant did not accumulate within the central necrotic region (P<0.01). This accumulation pattern was different from the WT strain, which accumulated in the necrotic region of cylindroids between 0<r/R<0.4 (FIG. 1C). The difference of these patterns suggests that WT *S. typhimurium*, with active Trg receptors, are attracted to purines and sugars, specifically ribose and galactose, which are released from degraded nuclei in the necrotic center of cylindroids.

Figure 4A:
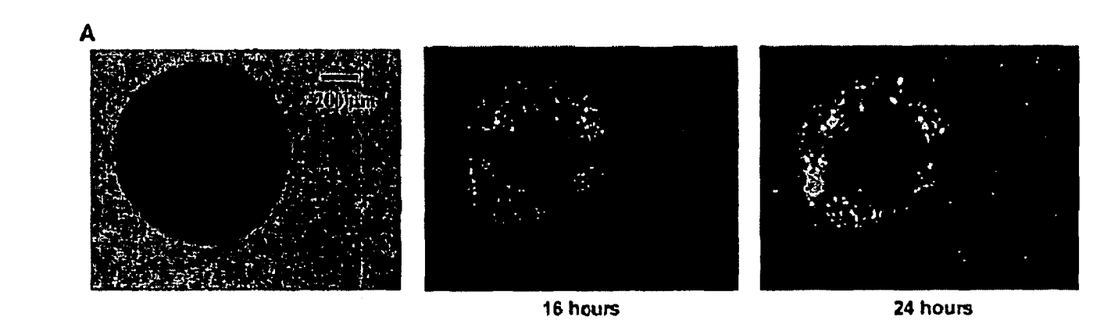
FIGS. 4A-D. A, time-lapse fluorescent microscopy images showing the accumulation pattern of the trg mutant in tumor cylindroid at 16 and 22 h after inoculation. B, average radial location (r/R=0.74±0.15) of trg colonies depicted in (A). Shaded area, region 1 SD wide around the mean location of colony formation ($n_{cylindroid}$=4; $n_{colonies}$=103). C, the area of trg colonies increased exponentially with a doubling time of 4.9 min ($n_{cylindroid}$=4; $n_{colonies}$=396). D, the number of trg colonies increased per cylindroid from 15 to 24 h ($n_{cylindroid}$=5).
Figure 4B:
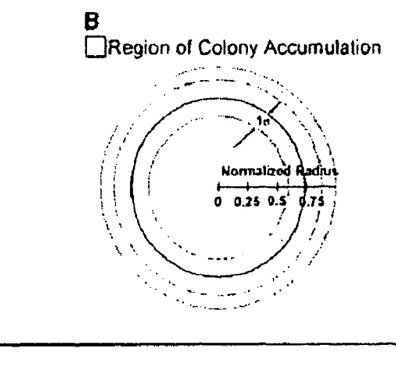
Figure 4C:
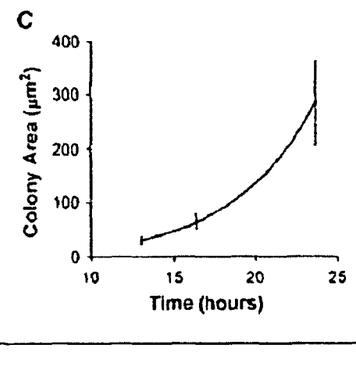
Figure 4D:
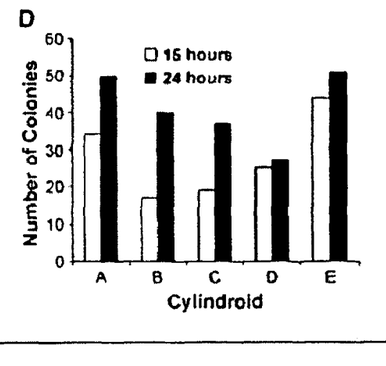
Figure 5A:
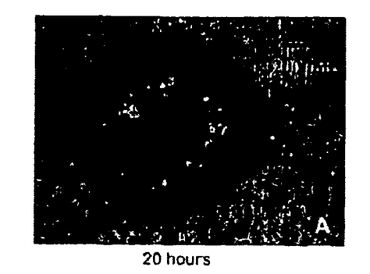
FIGS. 5A-D. A, fluorescent microscopy image showing the extent and location of trg accumulation (green) and the extent of apoptosis (red) in a tumor cylindroid 20 h after inoculation. The extent of apoptosis was detected using sulforhodamine conjugated to DEVD-FMK, a caspase-3 inhibitor that irreversibly binds to activated caspase-3 in apoptotic cells. B, fluorescence radial intensity profile showing the increase in caspase-3 expression in cylindroids between 3 and 20 h after inoculation with the trg mutant (n=6). Caspase-3 expression increased more in the center of cylindroids than at the edge. C, the average increase in caspase-3 activity per cylindroid was significantly greater for the WT and trg mutant than untreated controls (n=6). *, P<0.05. D, the increase in caspase-3 activity normalized by the bacterial intensity was significantly greater for the trg mutants compared with the WT (n=6). *, P<0.05.

Within cylindroids, the trg colonies increased in size and number over the duration of observation (FIG. 4A). The average growth of each colony was exponential with a doubling time of 4.9 h ($n_{colonies}$=396; $n_{cylindroids}$=4; FIG. 4C). This size increase was evidence of bacterial growth within cylindroids. The average number of colonies increased from 28±11 to 41±10 in the cylindroids between 15 and 24 h ($n_{cylindroids}$=5; FIG. 4D). The increase in colony number is an indication that chemotaxis continued throughout the experiment. In addition, trg did not form a ring of bacteria at the periphery of the cylindroids at early time points as observed in the WT (FIG. 1C).

Figure 5B:
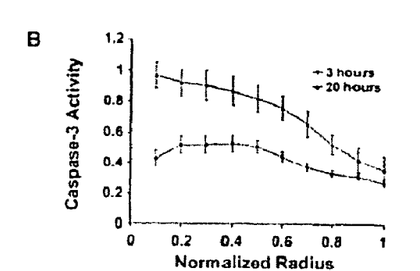
Figure 5C:
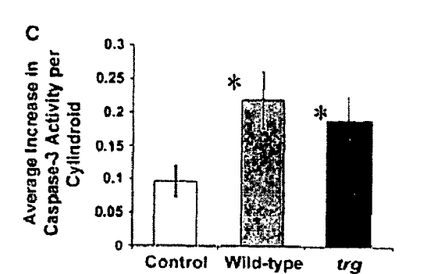
Figure 5D:
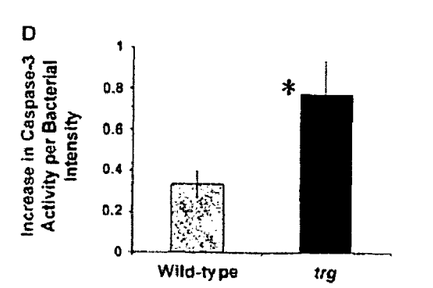

Accumulation of trg induces apoptosis in tumor cylindroids. Accumulation of the trg mutant induced tumor cell apoptosis in cylindroids (FIG. 5). The trg mutant localized to the expanding front of apoptotic cells in cylindroids (FIG. 5A). The activity of caspase-3, a mediator of mammalian cell apoptosis, increased between 3 and 20 h after inoculation with trg (n=6 per group; FIG. 5B). The extent of apoptosis increased more in the center of cylindroids than at the edge (FIG. 5B). The average increase of caspase-3 activity was significantly greater for both the WT and trg compared with untreated controls (P<0.05; n=6 per group; FIG. 5C). Compared with the WT, fewer bacteria accumulated in cylindroids inoculated with trg. When the caspase-3 activity was normalized by the average bacterial intensity, trg induced significantly more tumor cell apoptosis per bacterium than the WT (P<0.05; n=6; FIG. 5D). This difference between trg and the WT suggests that *S. typhimurium* strains that target quiescent regions of tumors will have an increased therapeutic effect over strains that preferentially colonize tumor necrosis.

Figure 6A:
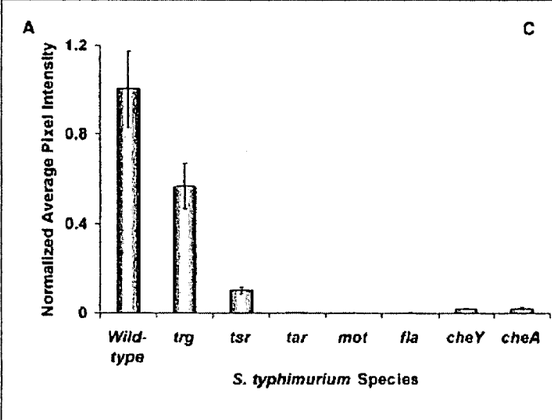
FIGS. 6A-D. A, total internal accumulation of all individual species of mutant *S. typhimurium* in tumor cylindroids at 24 h after inoculation (n=3). B, schematic representation of the individual roles of the chemoreceptors on chemotaxis and accumulation in tumor cylindroids. C, suggested chemoattractant gradient profiles located in tumor cylindroids that contain necrotic, quiescent, and proliferative regions. All concentrations are shown normalized to a maximum value inside cylindroids. D, projected accumulation pattern of WT and receptor knockouts (tar, tsr , and trg) *S. typhimurium* in heterogeneous tumor tissue surrounding a branched blood vessel. The tar mutant will remain in the blood vessel, the tsr mutant will not penetrate in the tumor tissue, the WT will accumulate in the necrotic region, and the trg mutant will accumulate in colonies within the quiescent region.

Overall internal accumulation of all *Salmonella* strains. To assess the overall extent of accumulation for each strain into tumor cylindroids, the average pixel intensity per area of cylindroid was calculated ($n_{cylindroid}$=24; FIG. 6A). The average pixel intensity represents the average bacterial concentration throughout the cylindroids at 24 h. The WT accumulated in cylindroids significantly more than any other strain (P<0.05). The trg and tsr mutants accumulated half and one tenth of the accumulation of the WT, respectively (P<0.01). The remaining mutant strains did not accumulate inside the tumor cylindroid at significant concentrations (P<0.01).

Figure 6B:
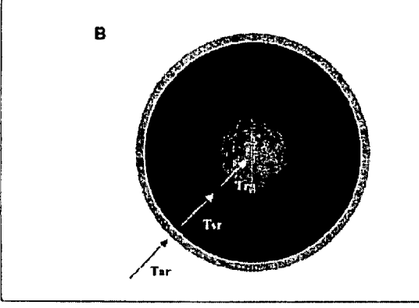

As shown, each component of the chemotaxis machinery was necessary for accumulation of *S. typhimurium* in tumor cylindroids, and each chemoreceptor directs *S. typhimurium* to different microenvironments within tumors. The Tar receptor caused migration of *S. typhimurium* to the edge of cylindroids, the Tsr receptor initiated penetration into cylindroids, and the Trg receptor directed *S. typhimurium* toward necrosis (FIG. 6B).

The signal transduction pathway and flagella machinery are necessary for chemotaxis toward tumor cylindroids. Chemotaxis was essential for accumulation of *S. typhimurium* in tumor cylindroids. General motility and properly constructed flagella were necessary for accumulation within tumor cylindroids (FIG. 1D). In the nonmotile mutants mot and fla, signals are correctly transmitted from the receptors through the cytoplasmic signal proteins, but improper functioning of the motor or lack of flagella filament prevents the bacteria from swimming up attractant gradients. Lack of accumulation in tumor cylindroids by these nonmotile mutants showed that chemotaxis, and not selective growth, is necessary to promote accumulation in tumors.

Figure 1A:
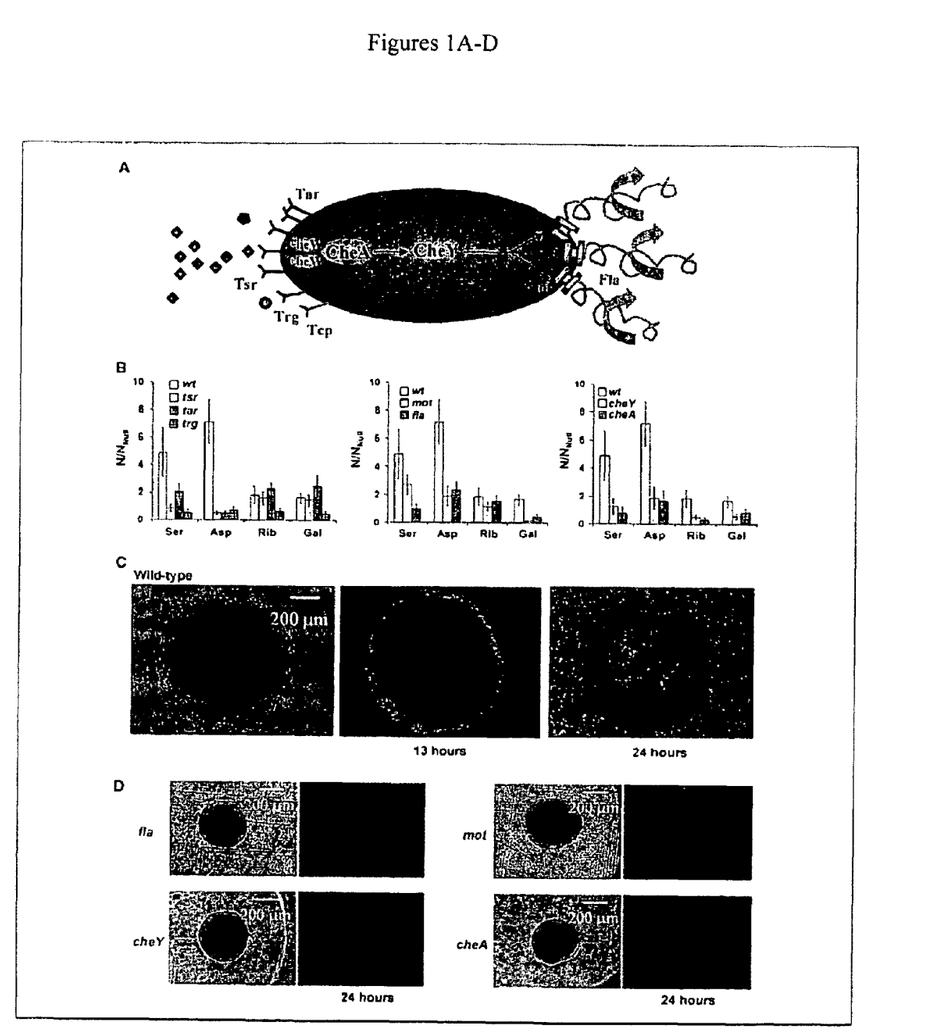
Figure 2A:
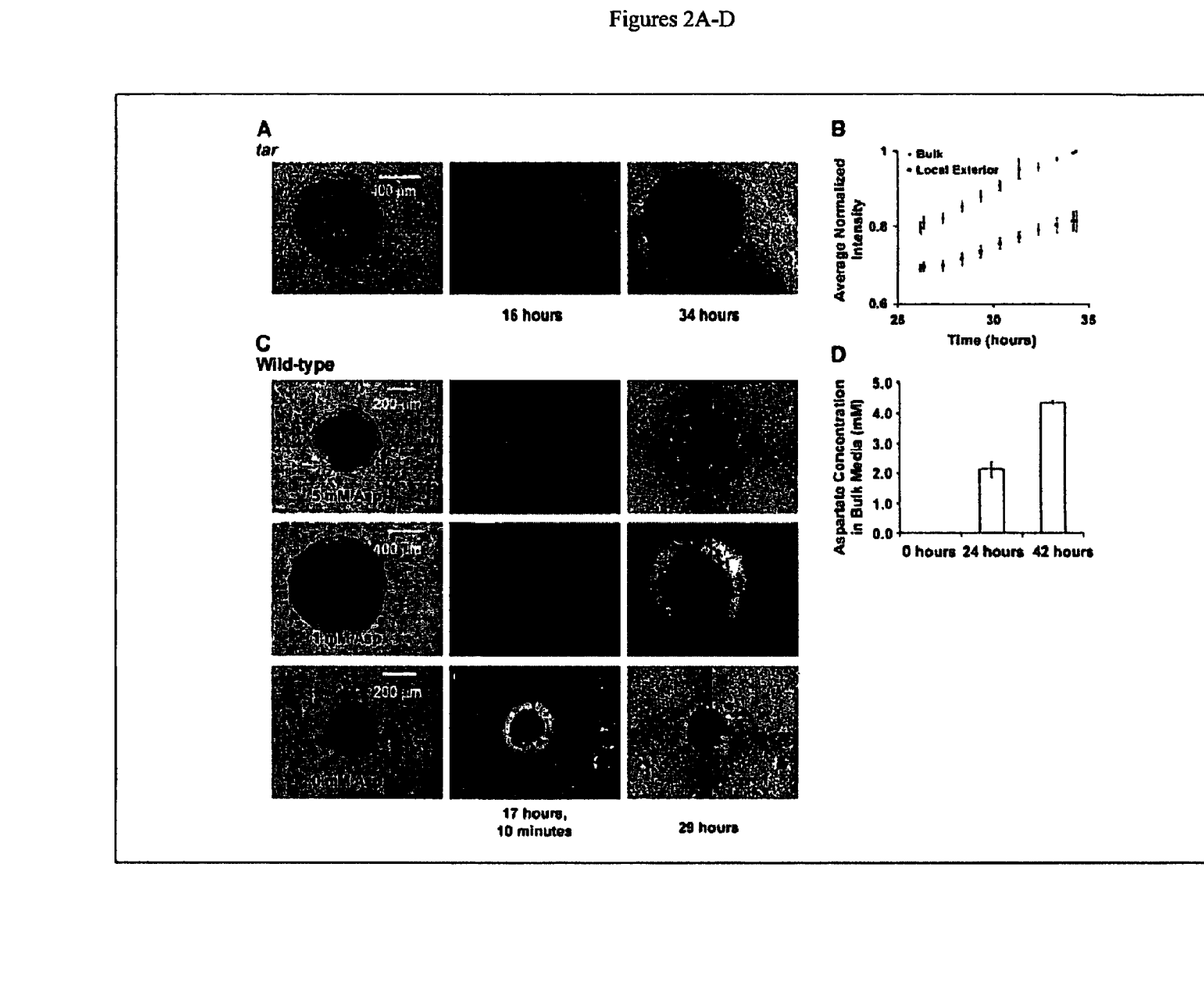

Complete functioning of the signal transduction pathway was also required for accumulation of *S. typhimurium* in tumor cylindroids (FIG. 1D). Without functioning signal transduction proteins (CheY and CheA), bacteria are motile but movement is not directed by attraction to chemoattractants (FIG. 1D). In the presence of an attractant gradient, the receptors bind attractant molecules, but a signal is not transmitted to the flagella (FIG. 1A) and the bacteria move randomly. The lack of accumulation of cheY and cheA showed that random bacterial motion did not contribute to *S. typhimurium* accumulation in tumor cylindroids.

Figure 6C:
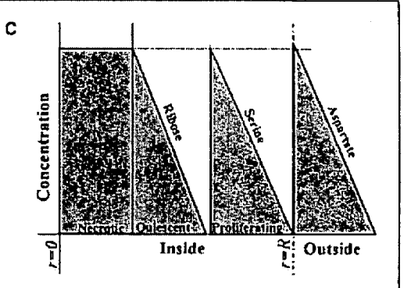

Chemoreceptors direct the accumulation of *S. typhimurium* toward specific microenvironments in tumors. Each chemoreceptor played a specific role in the chemotaxis of *S. typhimurium* in tumor cylindroids (FIG. 6B), and the accumulation pattern of each mutant suggests where chemoattractant gradients exist in cylindroids (FIG. 6C). Presence of the aspartate receptor was necessary for external chemotaxis toward tumor cylindroids, the serine receptor was necessary to initiate internal colonization of tumor cylindroids, and the ribose/galactose receptor directed bacteria into the central necrotic core of cylindroids (FIG. 6B). Results with the chemoreceptor knockouts further suggest that (a) an external aspartate gradient was present at the edge of cylindroids that attracted *S. typhimurium* to cylindroids, (b) a serine gradient existed in the cylindroid periphery that directed *S. typhimurium* penetration into cylindroids, and (c) a ribose/galactose gradient existed around the cylindroid center that attracted *S. typhimurium* into the necrotic core (FIG. 6C). The tar mutant, which has functional Tsr and Trg receptors, did not chemotax toward tumor cylindroids (FIG. 2), suggesting that neither a serine nor a ribose/galactose gradient existed away from the cylindroid edge into the bulk (FIG. 6C). The inability of tsr, which contains functional Trg receptors, to accumulate within cylindroids (FIGS. 3 and 6A) suggests that a ribose/galactose gradient did not exist at the periphery of cylindroids (FIG. 6C). The lack of central accumulation of the trg mutant (FIG. 5A) suggests that a ribose or galactose gradient existed around the cylindroid center, which may have been the result of the nuclear degradation of necrotic cells (FIG. 6C).

Figure 6D:
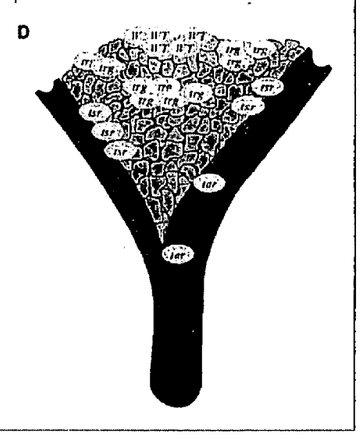

The interaction of the components of the chemotaxis machinery with chemoattractant gradients in cylindroids suggests how mutant *S. typhimurium* can accumulate in tumors in vivo. Because cancer cells grown as spheroids produced and excreted aspartate (FIG. 2D), an aspartate gradient may exist at the blood vessel lumen bordering in vivo tumors. In this environment, the tar mutant would not be attracted to a tumor and would remain in the blood vessel (FIG. 6D). Based on the chemoattractant gradients present in cylindroids (FIG. 6C), migration of *S. typhimurium* from blood vessels into tumors would be initiated by the Tsr receptor and accumulation in necrotic regions would be directed by the Trg receptor (FIG. 6D). A tsr mutant would remain in the tumor periphery, WT *S. typhimurium* would accumulate in necrotic regions, and a trg mutant would accumulate in quiescent regions (FIG. 6D), as demonstrated and as desired for a effective anti-cancer therapy.

EXAMPLES OF THE INVENTION

The following non-limiting examples and data illustrate various aspects and features relating to the compositions and/or methods of the present invention, including the treatment of various solid tumor cancer cell masses using methodologies of the sort described herein. In comparison with the prior art, the present methods and compositions provide results and data which are surprising, unexpected and contrary thereto. While the utility of this invention is illustrated through the use of several bacterial species and/or strains thereof, it will be understood by those skilled in the art that comparable results are obtainable with various other species/strains and various other solid tumor cancer cells and cellular masses, as are commensurate with the scope of this invention.

Materials and Methods.

Bacterial culture. Wild-type (WT; strain SL 1344, Aswad D, Koshland D E, Jr. Isolation, characterization, and complementation of *Salmonella typhimurium* chemotaxis mutants. J Mol Biol 1975; 95:225-35.) and all mutant strains of *S. typhimurium* were maintained in Luria broth and on agar plates using standard procedures. For visualization, all strains were transfected with a green fluorescent protein (GFP)-expressing, kanamycin- and ampicillin-resistant plasmid pSMC21 by electroporation with a Gene Pulser (Bio-Rad, Hercules, Calif.) according to the manufacturer's instructions. Electroporation variables were 1.8 kV, 200-Ω parallel resistance, and 25 μF capacitance.

Three strains of *S. typhimurium* were used to test the role of individual chemoreceptors. Strains ST326, ST328, and ST832 do not possess active tsr, tar, and trg genes, respectively, and were a kind gift from Dr. M. Eisenbach (The Weizmann Institute of Science, Rehovot, Israel). Each chemoreceptor of S. typhimurium does not function independently; one of the high-abundance chemoreceptors (Tsr or Tar) must be present to ensure proper functioning of the low-abundance Trg receptor, which has low methyl-accepting activity and limited ability to adapt to stimuli when it is the only receptor present in the cell. (Barnakov A N, Barnakova L A, Hazelbauer G L. Comparison in vitro of a high- and a low-abundance chemoreceptor of Escherichia coli: similar kinase activation but different methyl-accepting activities. J Bacteriol 1998; 180:6713-8.)

Four additional strains of S. typhimurium were used to test the role of other components of the chemotaxis machinery. Strains SJW2149 (fla), SJW3003 (mot), KK2014 (cheY), and KK2051 (cheA) were obtained from the Salmonella Genetic Stock Centre, University of Calgary (Calgary, Alberta, Canada). Strain SJW2149 (fla) does not produce the filament section of the flagella, and strain SJW3003 (mot) does not have functioning flagella motors and is incapable of rotating flagella. The enzymes CheA, a histidine kinase, and CheY, a response regulator, are key components of the signal transduction pathway (FIG. 1A), which controls bacterial chemotaxis by directing flagellar rotation in response to chemoattractant binding. Strain KK2014 (cheY) does not possess a functioning CheY protein and rotates its flagella in a counterclockwise direction exclusively, causing the bacteria to run in one direction, independent of chemoattractant gradients. Strain KK2051 (cheA) does not possess a functioning CheA and cannot regulate the flagella switch, which causes the bacteria to tumble randomly in their environment.

Example 1

Quantification of bacterial chemotaxis with the capillary assay. The ability of the mutant strains to chemotax toward chemoattractant molecules was quantified using the needle-syringe capillary assay developed by Mazumder et al. (Mazumder R, Phelps T J, Krieg N R, Benoit R E. Determining chemotactic responses by two subsurface microaerophiles using a simplified capillary assay method. J Microbiol Methods 1999; 37:255-63.) Cultures of the mutant strains were grown to midlogarithmic phase, centrifuged, washed, and suspended in motility buffer to a final concentration of $3.2 \times 10^7$ bacteria/mL. Hypodermic needles (25 gauge) attached to 1 mL syringes (Becton Dickinson, Franklin Lakes, N.J.) were filled with 0.1 mL of chemoattractant solution containing 0.1 mmol/L serine, 1 mmol/L aspartate, 1 mmol/L ribose, or 1 mmol/L galactose. These concentrations known in the literature as optimum for chemotaxis. The needle-syringe assemblies were inserted into 200 µL pipette tips containing the bacterial suspension and incubated at 35° C. for 1 h. After incubation, the content of the needles was removed, diluted, and plated to quantify the number of colony-forming units (CFU). For each strain and each attractant, 27 plates were used. Chemotactic ability, $N/N_{Null}$, was reported as the ratio of the average number of bacteria that accumulated in the chemoattractant capillaries to the average number of bacteria that accumulated in the chemoattractant-free controls.

Example 2

Mammalian cell culture. LS174T colon carcinoma cells were grown in DMEM with 10% fetal bovine serum (FBS) and 26 mmol/L HEPES buffer at 37° C. and 5% $CO_2$. Cell aggregates were grown in tissue culture flasks coated with 20 mg/mL poly(2-hydroxyethyl methacrylate) for 9 days to form spheroids.

Example 3

Cylindroid formation. Formation of tumor cylindroids was done as described previously. (Kasinskas R W, Forbes N S. Salmonella typhimurium specifically chemotax and proliferate in heterogeneous tumor tissue in vitro. Biotechnol Bioeng 2006; 94:710-21.) Briefly, cylindroids were formed by constraining spheroids between the bottom surface of a 96-well plate and the top surface of a set of polycarbonate cylindrical plugs attached to a polycarbonate lid with a gap width of 150±5 µm. The diameter of each cylindroid was dependent on the initial size of the spheroid used in its formation. Spheroids ranging from 150 to 1,000 µm in diameter were selected based on their size, symmetry, and overall integrity. After being constrained, cylindroids were allowed to equilibrate for 22 h in 100 µL DMEM to relieve mechanical stress and establish oxygen and metabolic gradients before subjection to further experimentation.

Example 4

Bacterial inoculation into cylindroids. Before inoculation into cylindroid cultures, all strains were grown at 37° C. to midlogarithmic phase ($A_{600}$ 0.3-0.5) from single colony cultures. Individual colonies were chosen from agar plates following confirmation of GFP expression using fluorescence microscopy. Bacterial cultures were centrifuged at 4,000 rpm for 10 min and resuspended in DMEM (Sigma-Aldrich, St. Louis, Mo.) with 10% FBS (Sigma-Aldrich) and 26 mmol/L HEPES buffer (Invitrogen, Carlsbad, Calif.) to a final concentration of 500 CFU/mL. Equilibrated cylindroid cultures were inoculated with 100 µL of 500 CFU/mL S. typhimurium. Time-lapse fluorescent images were acquired at 10-min intervals up to 34 h after inoculation. Excitation light was shuttered between acquisitions to prevent photobleaching.

To test the influence of aspartate on the behavior of WT S. typhimurium accumulation, cylindroids were prepared as described previously, except cylindroids were equilibrated in medium containing 1 or 5 mmol/L of added aspartate. Bacteria added to the cylindroids were suspended in medium containing corresponding concentrations (1 or 5 mmol/L) of aspartate.

Example 5

Image acquisition and analysis. The accumulation of bacteria and fluorescent dyes in cylindroids was quantified using time-lapse microscopy as described previously. (Kasinskas and Forbes, supra.) An automated stage and image acquisition macro were used to acquire multiple images centered on each cylindroid for multiple days. For each cylindroid, four images (size: 665.8 µm×873.9 µm) were acquired with a 10× objective and tiled together. Fluorescence intensity inside cylindroids was measured as a function of both position and time. The radius of cylindroids was determined from transmitted light images. Radial profiles were generated from the fluorescent images by averaging all of the pixel intensities at a series of radii from the cylindroid center (r=0) to the cylindroid edge (r=R) using a script in ImageJ (NIH Research Services Branch). To account for the effects of autofluorescence, the radial profile at the initial time was subtracted from the profiles.

Example 6a

Analysis of bacterial localization in cylindroid cultures. The chemotactic behavior of the WT and chemoreceptor mutants was quantified by averaging and comparing the fluorescent intensities of different regions in multiple cylindroids. Regions were defined relative to the individual centers and edges of cylindroids. The use of relative distances enabled comparison of multiple cylindroids of different size and the establishment of statistical significance among populations of similar cylindroids.

Example 6b

The growth of the tar mutant in cylindroid cultures was determined by measuring the change in fluorescence intensity in the bulk and in the region directly outside the cylindroids as a function of time. For this measurement, the bulk region was defined as a 400 $\mu m^2$ area at least 200 $\mu m$ from the cylindroid edge. The periphery region was defined as an annulus 200 $\mu m$ in radius around the outside of the cylindroid.

Example 6c

The extent of central accumulation of the tsr mutant was quantified by comparing the average fluorescence intensity in the cylindroid center to the intensity at the leading edge of the bacterial ring. The cylindroid center was defined as a circular region with a radius equal to 20% of the cylindroid radius. The bacterial ring was defined as an annulus of pixels with a thickness equal to 20% of the cylindroid radius and centered on the circle of maximum fluorescence intensity. Data were normalized to the maximum pixel intensity of the bulk at the final time point (t=26 h).

Example 6d

The size and location of trg colonies in cylindroids were determined using particle analysis in ImageJ. The number of colonies was measured as a function of time, and the location of each colony was determined relative to the center and outside edge of the cylindroids. When counting colonies, a group of two or more bacteria was considered a colony. To exclude single bacterium, the minimum area of an acceptable particle was set at 13 pixels. This value was chosen based on the maximum possible area occupied by two bacteria that are 1.0 $\mu m$ in diameter and 2.0 $\mu m$ in length.

Example 6e

The overall accumulation of each strain was determined by measuring the average pixel intensity inside the cylindroid boundary at 24 h and normalizing to the average pixel intensity of the WT.

Example 7

Quantification of aspartate produced by spheroids. To quantify the amount of aspartate produced by spheroids, 100 $\mu L$ samples were taken from three spheroid cultures at 0, 24, and 42 h after changing the medium. Spheroids were grown in spinner flasks to an average diameter of 715 $\mu m$ and a density of ~20 spheroids/mL. The aspartate concentration was measured according to literature methods. Each sample was lyophilized overnight and dissolved in 100 $\mu L$ of dimethylformamide and 100 $\mu L$ of N-methyl-N-(tert-butyldimethylsilyl) trifluoroacetamide containing 1% tert-butyldimethylchlorosilane at 70° C. for 1 h to produce tertbutyldimethylsilyl amino acid derivatives. Gas chromatography-mass spectroscopy analysis was done using an Agilent 6890 with a 30 m×0.25 mm, 0.25-$\mu$Am film thickness, DB-5 capillary column (Supelco, Bellefonte, Pa.) and a Micromass gas chromatography time-of-flight mass spectrometer. The injector temperature, detector temperature, and injection volume were 300° C., 280° C., and 10 $\mu L$, respectively. The oven temperature was ramped from 140° C. to 255° C. at 3° C. per minute to completely separate metabolites. The relative molar concentration of aspartate in each sample was calculated from standard curves with standards of known concentration.

Example 8

Quantification of apoptotic cells. The extent of apoptosis was measured in cylindroids using the CaspGLOW Red Caspase-3 Staining kit (BioVision, Inc., Mountain View, Calif.). This assay uses DEVD-FMK, an inhibitor that irreversibly binds to activated caspase-3, conjugated to sulforhodamine (Red-DEVD-FMK). To stain for apoptotic cells, 100 $\mu L$ of 1:1,000 (v/v) Red-DEVD-FMK in DMEM was added to each cylindroid-containing well. The cylindroids were incubated in staining solution at 37° C. and 5% $CO_2$ for 2 h. The staining medium was not removed before imaging because it is nontoxic to mammalian cells. The location of apoptosis was determined by generating radial intensity profiles of cells stained with Red-DEVD-FMK. The fluorescence intensity was normalized to the maximum pixel intensity at the final time point (20 h). The average increase in caspase-3 activity was determined by subtracting the average Red-DEVD-FMK intensity throughout the entire cylindroid at 3 h from the average intensity at 20 h after inoculation. The extent of apoptosis induced per individual bacterium was determined by normalizing the average difference in caspase-3 activity at 3 and 20 h by the average bacterial intensity throughout the cylindroids.

Control of bacterial accumulation in cancer cell masses and/or tumors can be achieved by selectively eliminating chemoreceptor genes from therapeutic *S. typhimurium* strains. The trg knock-out mutant is useful with respect to the methods and/or compositions of this invention, as it accumulates in the therapeutically inaccessible, quiescent region and showed a greater individual effect on inducing apoptosis than the WT. This mutant is attracted to tumors, can penetrate into tumor tissue, but does not preferentially colonize tumor necrosis. Such behaviors can be used effectively to colonize quiescent regions of tumors otherwise unaffected by standard cancer therapies.

We claim:
1. A method of treating a solid tumor cancer cell mass, said method comprising:
   providing a non-pathogenic mutant *Salmonella* bacteria species, wherein said species is a strain absent a gene for tumor necrosis chemoreception, and wherein said strain is capable of chemotaxis to a quiescent region of a tumor cell mass; and
   contacting a solid tumor cancer cell mass with said bacteria species.
2. The method of claim 1 wherein said strain is absent an active trg gene.
3. The method of claim 1 wherein said species is a non-pathogenic strain of *S. typhimurium*.
4. The method of claim 3 wherein said strain is absent an active trg gene.
5. The method of claim 1 wherein said contact is in vivo.
6. The method of claim 5 wherein said cell mass is of a human solid tumor cancer characterized by ribose and galactose necrotic cell nuclear degradation products.

7. The method of claim 6 comprising bacterial accumulation in a quiescent region of said mass, with increased apoptosis compared to a wild-type *Salmonella* species.

8. A method of using bacterial chemotaxis to treat a human solid tumor cancer, said method comprising:
   providing a human solid tumor cancer cellular mass comprising a quiescent region of said mass; and
   contacting said mass with a non-pathogenic mutant *Salmonella* bacteria species, wherein said species is a strain absent an active Trg chemoreceptor, and wherein said bacteria accumulate in a quiescent region of said mass.

9. The method of claim 8 wherein said species is a non-pathogenic strain of *S. typhimurium*.

10. The method of claim 8 wherein said contact is in vivo.

11. The method of claim 8 comprising monitoring caspase-3 activity within said mass.

12. The method of claim 11 comprising bacterial accumulation in a quiescent region of said mass, with increased cellular apoptosis compared to a wild-type *Salmonella* species.

13. A method of inducing human solid tumor cancer apoptosis, said method comprising:
   providing a human solid tumor cancer cellular mass comprising a quiescent region of said mass; and
   contacting said mass with a non-pathogenic mutant strain of *S. typhimurium*, wherein said strain is absent an active Trg chemoreceptor, and wherein said bacterial strain accumulates in a quiescent region of said mass.

14. The method of claim 13 comprising monitoring caspase-3 activity within said mass.

15. The method of claim 14 comprising accumulation of said strain in a quiescent region of said mass, with increased apoptosis compared to a wild-type *Salmonella* species.

16. A method of treating a colon cancer cell mass, said method comprising:
   providing a non-pathogenic mutant *Salmonella* bacteria species, wherein said species is a strain absent a gene for tumor necrosis chemoreception, said strain is capable of chemotaxis to a quiescent region of a tumor cell mass; and
   contacting a colon cancer cell mass with said bacteria species.

17. The method of claim 16 wherein said species is a non-pathogenic strain of *S. typhimurium*.

18. The method of claim 17 wherein said strain is absent an active trg gene.

19. The method of claim 16 wherein said cell mass is characterized by ribose and galactose necrotic cell nuclear degradation products.

20. The method of claim 19 comprising bacterial accumulation in a quiescent region of said mass, with increased apoptosis compared to a wild-type *Salmonella* species.

* * * * *